United States Patent
Campin et al.

(10) Patent No.: US 7,665,846 B2
(45) Date of Patent: *Feb. 23, 2010

(54) DETERMINING OPTIMAL POSITIONING OF OPHTHALMIC DEVICES BY USE OF IMAGE PROCESSING AND AUTOFOCUSING TECHNIQUES

(75) Inventors: John A. Campin, Orlando, FL (US); John J. Bowes, Orlando, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 354 days.

This patent is subject to a terminal disclaimer.

(21) Appl. No.: 11/614,624

(22) Filed: Dec. 21, 2006

(65) Prior Publication Data
US 2007/0153233 A1    Jul. 5, 2007

Related U.S. Application Data

(60) Provisional application No. 60/755,556, filed on Dec. 31, 2005.

(51) Int. Cl.
*A61B 3/14* (2006.01)

(52) U.S. Cl. .................. 351/208; 351/206; 351/246; 606/5

(58) Field of Classification Search .................. 351/208
See application file for complete search history.

(56) References Cited

U.S. PATENT DOCUMENTS

| | | | |
|---|---|---|---|
| 6,532,298 | B1 | 3/2003 | Cambier et al. |
| 2004/0263786 | A1* | 12/2004 | Williams et al. ............ 351/246 |
| 2005/0105044 | A1 | 5/2005 | Warden et al. |
| 2006/0119794 | A1* | 6/2006 | Hillis et al. .................. 351/205 |
| 2006/0244907 | A1* | 11/2006 | Simmons .................... 351/162 |
| 2007/0027442 | A1* | 2/2007 | Campin et al. ................ 606/12 |

FOREIGN PATENT DOCUMENTS

| | | |
|---|---|---|
| EP | 1422923 | 5/2004 |
| EP | 1437085 A1 | 7/2004 |
| GB | 2359375 | 8/2001 |

\* cited by examiner

*Primary Examiner*—Jessica T Stultz
(74) *Attorney, Agent, or Firm*—Armando Pastrana, Jr.

(57) ABSTRACT

A system or method of positioning an ophthalmic device relative to an eye is provided. The method first obtains a series of images of an eye. In these series of images, the distance between the ophthalmic device and the eye is varied while the region of the eye image remains substantially the same. It is possible then to process these images to determine the high frequency content associated with each image. By comparing the high frequency content associated with each image, it is possible to determine which image has the largest amount of high frequency content. The high frequency content is maximized when the image is the sharpest. An optimally focused image will have the largest amount of high frequency content. By examining the high frequency content associate with the series of images is impossible to adjust the relative position and distance between the eye and the ophthalmic device to the distance associated with the image having the largest amount of high frequency content (i.e., optimally focused).

12 Claims, 13 Drawing Sheets

DETERMINING OPTIMAL POSITIONING OF OPHTHALMIC DEVICES BY USE OF IMAGE PROCESSING AND AUTOFOCUSING TECHNIQUES

CROSS-REFERENCE TO RELATED APPLICATIONS

This application claims priority under 35 U.S.C. §119 to U.S. Provisional Patent Application No. 60/755,556, filed Dec. 31, 2005, the entire contents of which are incorporated herein by reference.

TECHNICAL FIELD OF THE INVENTION

The present invention relates generally to ophthalmic devices, and more particularly, to a system and method for determining optimal positioning of ophthalmic devices.

BACKGROUND OF THE INVENTION

Positioning an ophthalmic device a known distance from an eye being examined is typically of great importance. In many devices one reason for this precise positioning is to have features of the eye in clear focus—potentially for subsequent interaction with the image by an operator or software. Other reasons include the need to have a laser beam come to focus at the correct plane with respect to the eye (for example in an excimer laser system) or to have the eye optimally positioned for subsequent measurement of the eye (for example a wavefront measurement).

A number of techniques are used to assist in eye-to-device positioning. These include the breaking of light beams (usually IR) by the corneal apex and the projection onto the cornea of a number of light beams, which can subsequently be analyzed either automatically or by an operator to assess accuracy of eye positioning. If the eye is deemed to not be in the optimal position then the device and/or head/eye can be moved so as to reposition the eye optimally or to within defined acceptable tolerances.

The application of lasers and other like ophthalmic devices to diagnose conditions of the eye has opened new possibilities for treating nearsightedness, farsightedness, astigmatism, and other conditions of the eye. Specifically, Laser technology has allowed the development of modern laser techniques that are collectively known as laser vision correction.

Laser vision correction techniques reshape the surface or subsurface of eye 10 as shown in FIG. 1. These techniques may employ a cool beam of light (such as Excimer laser beam 12) to remove microscopic amounts of tissue. The removal of this tissue changes the shape of cornea 14 in order to allow sharper focusing of images and reducing a patient's dependence on glasses and/or contact lenses. Laser vision correction surgeries include, but are not limited to, laser-assisted in situ keratomileusis (LASIK), laser epithelial keratomileusis (LASEK), epi-LASIK, automated lamellar keratoplasty (ALK), photo ablation procedures such as photo refractive keratectomy (PRK), and other like procedures.

In these procedures, the quality of the results of the laser vision correction may depend upon the ability of the laser 12 to precisely remove tissue from the surface or beneath the surface of cornea 14. Accurately removing tissue with laser 12, in turn may at least in part depend on the ability to accurately align and position the laser and other imaging systems with reference to the eye undergoing the procedure.

One of the most time consuming portions of the procedure is the set up and positioning of the laser. Existing procedures may utilize manual techniques to align the laser prior to the laser vision correction. Additionally, laser vision correction procedures often require alignment of the laser between individual patient's procedures or between an individual patient's eyes. Also, there may be a need to determine the positioning of the device during the procedure.

SUMMARY OF THE INVENTION

Embodiments of the present invention provide a system and method operable to position an ophthalmic device relative to an eye that substantially addresses the above identified needs as well as other needs. One embodiment provides a method which first obtains a series of images of an eye. In the series of images, the distance between the ophthalmic device and the eye is varied while the region of the eye image remains substantially the same. The images are then processed to determine a high frequency content or sharpness function associated with each image. By comparing the high frequency content associated with each image, the image having the largest amount of high frequency content or highest sharpness function is identified. The high frequency content or sharpness function varies with the focus of the image. An optimally focused image will have the largest amount of high frequency content or highest sharpness function. By identifying the image associated with the highest frequency content or sharpness function from the series of images, the relative position or distance between the eye and the ophthalmic device having the largest amount of high frequency content (i.e., optimally focused) is identified. This distance may be used to position the ophthalmic device relative to the patient's eye.

In another embodiment, the present invention provides an ophthalmic device positioning system. This ophthalmic device positioning system includes an image gathering system, a processing system, and a positioning system. The image gathering system gathers a series of images of an eye wherein a relative distance between the image gathering system and the eye vary. The processing system couples to the image gathering system, and is operable to perform a sharpness function on each of the gathered images. The results of the sharpness functions are compared in order to identify the image associated with the highest sharpness function. As previously stated, image focus is optimized within the image having the highest sharpness function. Thus, the relative distance between the image gathering system and the eye for the image associated with the highest sharpness function may be identified. The positioning system is operable to match an actual distance between an ophthalmic device and the eye to the relative distance between the image gathering system and the eye from the image associated with the highest sharpness function.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the FIGs., like numerals being used to refer to like and corresponding parts of the various drawings.

Figure 1:
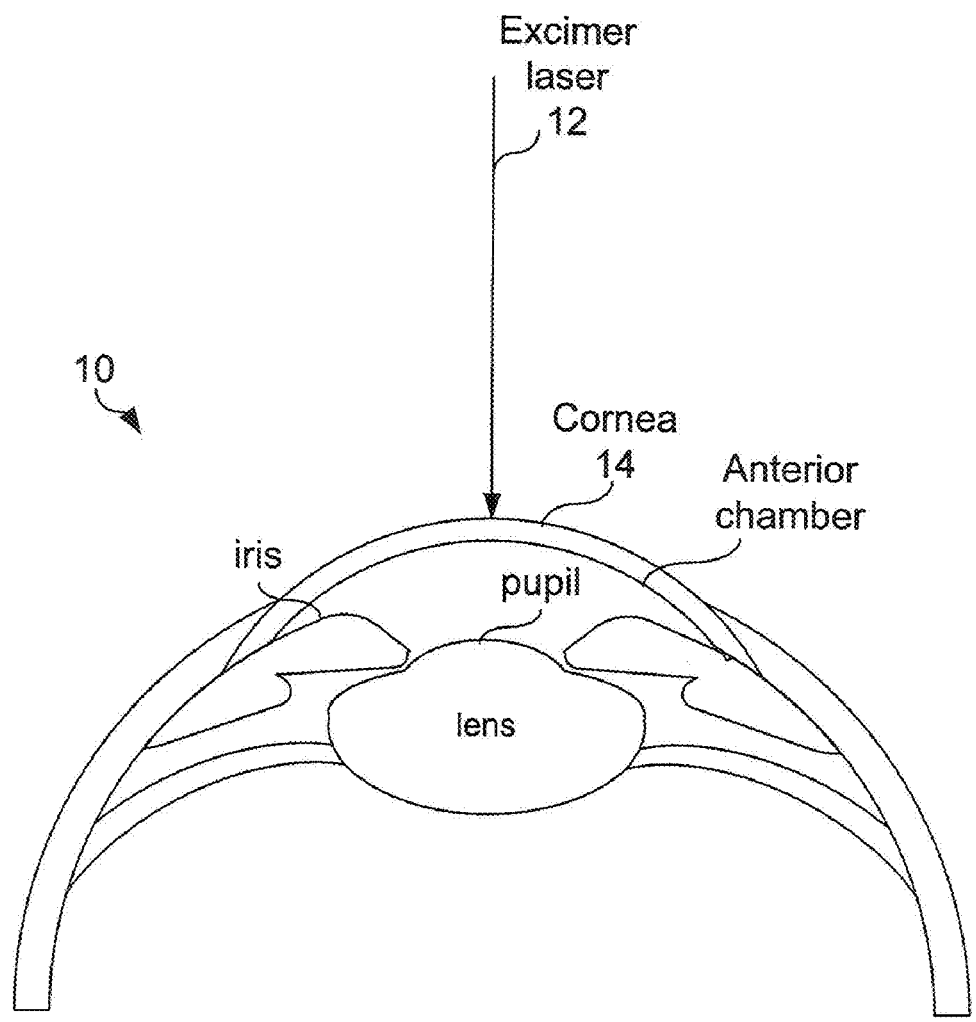
FIG. 1 provides an overview of a laser vision correction surgical procedure where an Excimer laser beam is used to reshape a patient's cornea.
Figure 2:
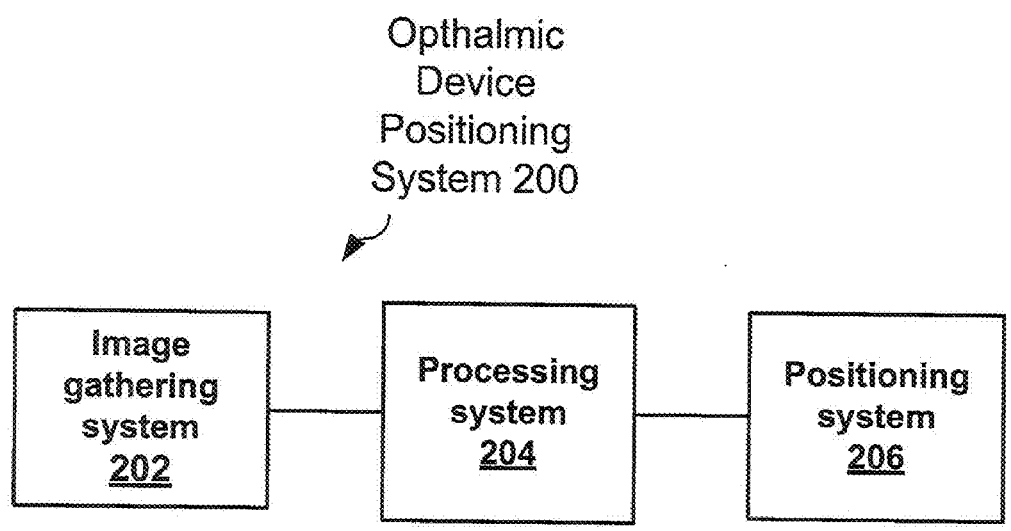
FIG. 2 provides an ophthalmic device positioning system in accordance with an embodiment of the present invention.

FIG. 2 provides an ophthalmic device positioning system 200. Ophthalmic device positioning system 200 includes an image gathering system 202, a processing system 204, and a positioning system 206. The image gathering system 202 may be a camera or a video device operable to gather a series of images of the eye. Image gathering system 202 is operable to record relative distance between the image gathering system 202 and the eye where the image is gathered. The processing system 204, as will be discussed in further detail, receives the images gathered and performs a sharpness function on each of the gathered images.

The processing system 204 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the system controller implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the system controller executes, operational instructions corresponding to at least some of the steps and/or functions illustrated in FIGS. 2, 4 and 5 associated with embodiments of the present invention.

After performing the sharpness function, a comparison of the sharpness function results may identify an image associated with the highest sharpness function. As will be explained, with reference to FIG. 4 and following, image focus may be optimized within the image having the highest sharpness function. After identifying the image associated with the highest sharpness function, the relative distance between the eye and image gathering system may be identified. This distance is used to position the device to achieve an optimized focus for the ophthalmic device. The positioning system 200, either automatically or through a series of prompts to an operator of a manually aligned system, facilitates the positioning of the ophthalmic device relative to the eye. Relative positioning of the ophthalmic device to the eye may involve repositioning the ophthalmic device or repositioning the patient's eye.

Figure 3:
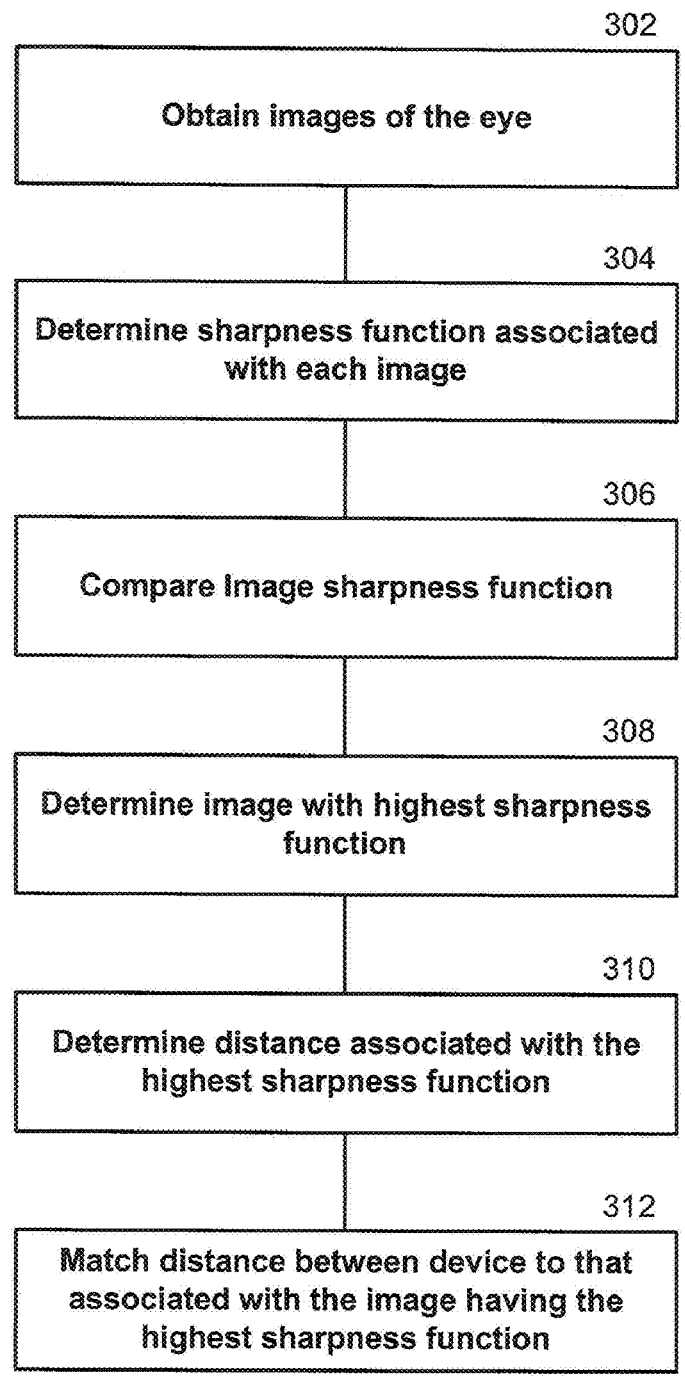
FIG. 3 provides a logic flow diagram of a method of positioning an ophthalmic device relative to an eye in accordance with an embodiment of the present invention.

FIG. 3 provides a logic flow diagram of an embodiment of the method of the present invention for positioning an ophthalmic device relative to an eye. This embodiment includes first obtaining a series of images of an eye, wherein the ophthalmic device and eye are separated by a different distance for each image. However, the same region of the eye should be contained within a substantially similar region within each image. This series of images are obtained in step 302. In step 304, a sharpness function as will be described with respect to FIG. 4 and following may be determined for each image. In step 306, the sharpness function associated with each image is compared to determine which image has the highest sharpness function. Step 308 identifies the image having the highest sharpness function. This image corresponds to the image having the best focus for the set of images. Lastly, the embodiments of the present invention are able to determine the distance between the ophthalmic device and the eye having the best focus. Other embodiments may further include adjusting the distance between the ophthalmic device and the eye to match the distance associated with the highest sharpness function in step 312.

Embodiments of the present invention described herein maybe deployed to existing systems where image gathering systems already exist and are operable to obtain images of the surface of the eye. Such image gathering systems may include, but are not limited to, a video camera or frame grabber.

A well-focused image of the eye has relatively sharp edges. For example, the blood vessels in the sclera or features of the iris are most clearly defined when the image is in good focus. When the image is somewhat out of focus the image is softened and the edges of these features are less clear. When the image has more clearly defined edges, then the amount of high frequency information or sharpness in the image is higher.

A number of sharpness functions exist and numerically describe this effect. These functions include, but are not limited to, estimates of image gray level variance and amplitude, computation of the intensity difference between adjacent pixels, histogram-based approaches, standard edge-detection masks such as "Laplacian" and functions based upon Fourier transforms. Each technique has unique advantages and disadvantages. For example, Fourier Transform based approaches yield a large amount of detailed data and very sophisticated functions can be developed and fine-tuned to optimally address a defined problem. However, Fourier transforms of large images are computationally intensive and can incur a relatively large amount of time to perform this processing. Conversely, simple pixel intensity difference functions (F), such as that given by equation 1, have relatively minimal computational issues but lack the flexibility of a Fourier based approach. Depending upon the specific implementation details and requirements, different functions may be preferred. Details impacting the choice of function include attributes of the image, the frequency with which the calculations need to be performed and accuracy requirements.

$$F = \sum |I(x, y) - I(x, y-1)| + \sum |I(x, y) - I(x, y+1)|. \qquad \text{EQ 1}$$

Although a Fourier based implementation is more detailed, the present invention may employ any known sharpness function.

Computing a Fourier transform (typically via a Fast Fourier Transform (FFT)) of the area or areas of the image of interest, determines the amount of information present in the higher spatial frequencies. By setting the device-to-eye distance such that the high spatial frequency content is maximized, focus can be optimized. Hence, the distance between the ophthalmic device and the eye can be optimized.

In cases where instrument positioning is automated, this distance information may be used as the basis for automatically positioning the ophthalmic device such that the ophthalmic device is located at an optimal distance from the eye. If automated positioning is not possible, then this information can be used to provide indicators, by means of a user interface or audible cues—to assist in the positioning of the ophthalmic device.

Although a primary benefit may be to optimally position a device prior to a procedure (surgical or otherwise), the embodiments of the present invention may also be used during the subsequent procedure to verify proper setup and halt the procedure when specific thresholds are exceeded. The same basic approach can be used to check that the eye remains the appropriate distance from the device, and optimally reposition the ophthalmic or other like eye related device during the procedure.

One should note that typical autofocus mechanisms are normally employed to bring an object into good focus by adjusting parameters or features of the device employing the autofocus mechanism. In these typical mechanisms, the distance to the object of interest is not adjusted. The present invention differs in that here the opposite is true. The distance to the object of interest (in this case, the eye) must be adjusted so as to be the optimal distance from the device.

A secondary consideration is controlling the position of the eye within the field of view of the device. Customarily, ophthalmic devices are adjusted in left-right and up-down directions so as to optimally align an ophthalmic device with respect to an eye. Using software processing of an image of the eye, a user can automatically determine the location of the pupil or other like feature within the eye. Once those features are identified, the motion required to optimally align the device and eye is computed. This motion can be accomplished automatically or manually be adjusting the position of the ophthalmic device itself or, if the patient is in a chair or bed, by adjusting the position of the chair or bed. Several techniques may be used to locate the eye within the field of view, including, but not limited to, iris boundary detection, and pupil location detection. As an example, a method for identifying the pupil location is discussed below. In the example discussed below, the image is scanned such that the darkest region in the image is found so as to determine the approximate pupil center, and then more sophisticated pupil boundary processing is performed so as to refine this estimate.

Figure 4:
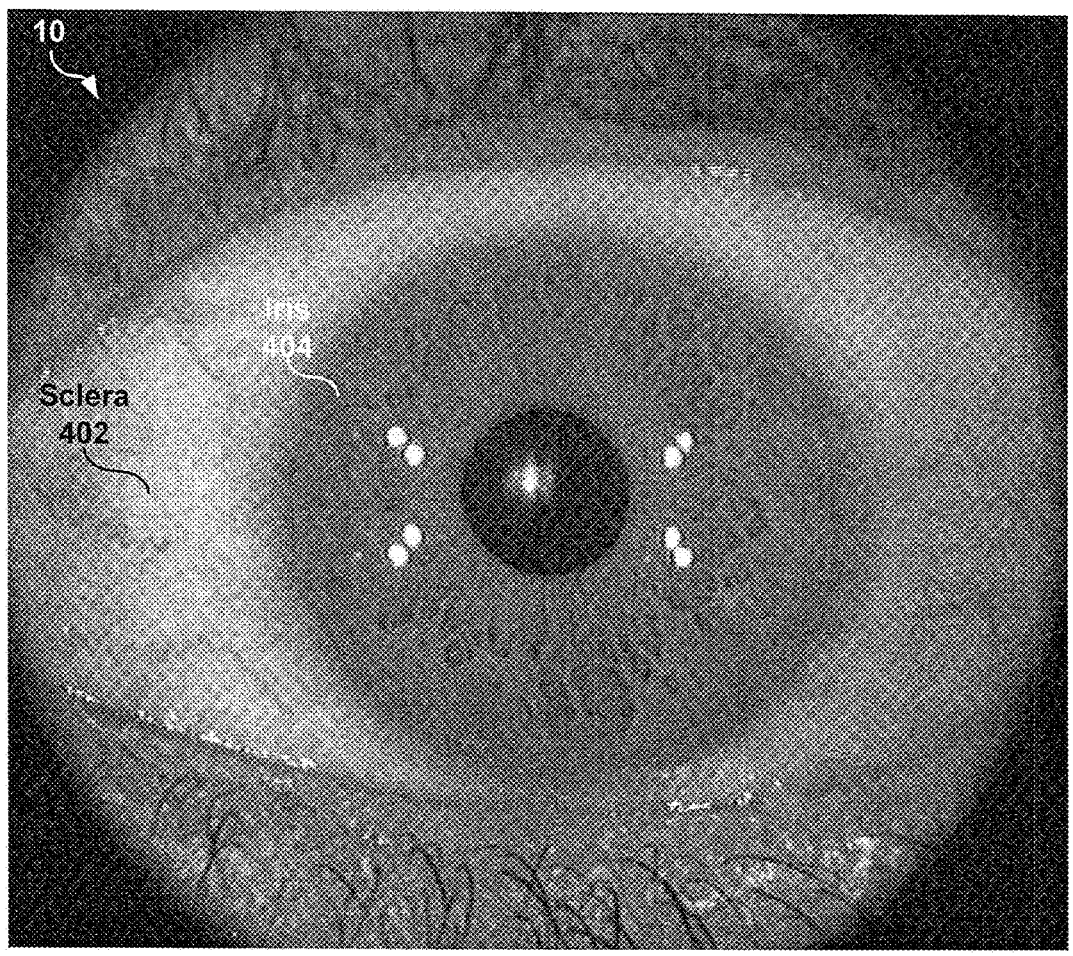
FIG. 4 shows a typical image of an eye captured on a wavefront sensor.
Figure 5A:
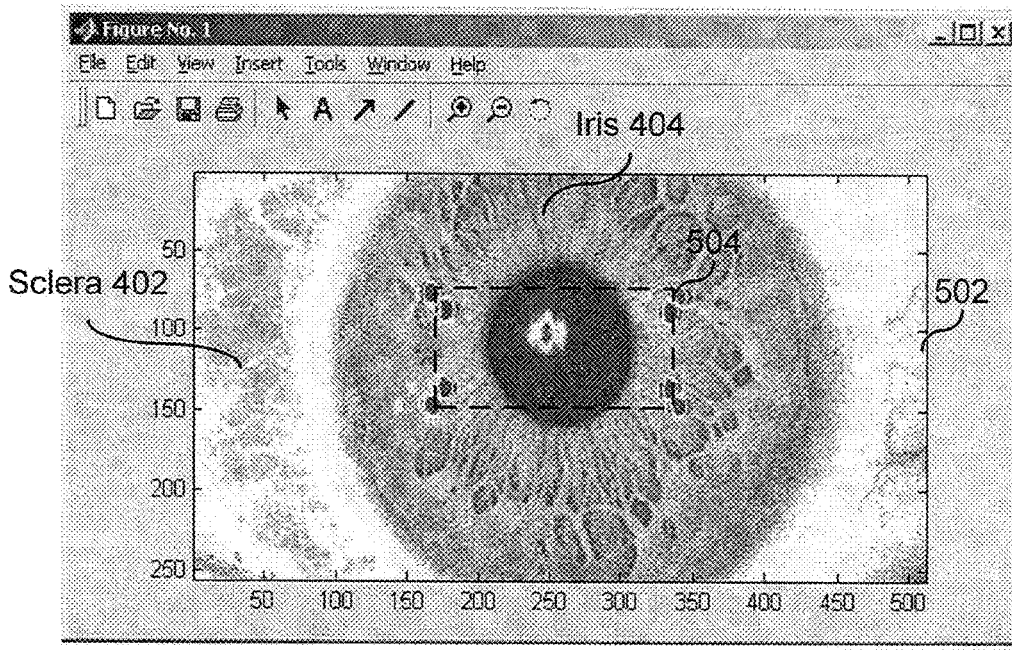
FIGS. 5A, 6A, 7A, 8A and 9A mimic the effect of defocus caused by having the eye in the wrong position.
Figure 5B:
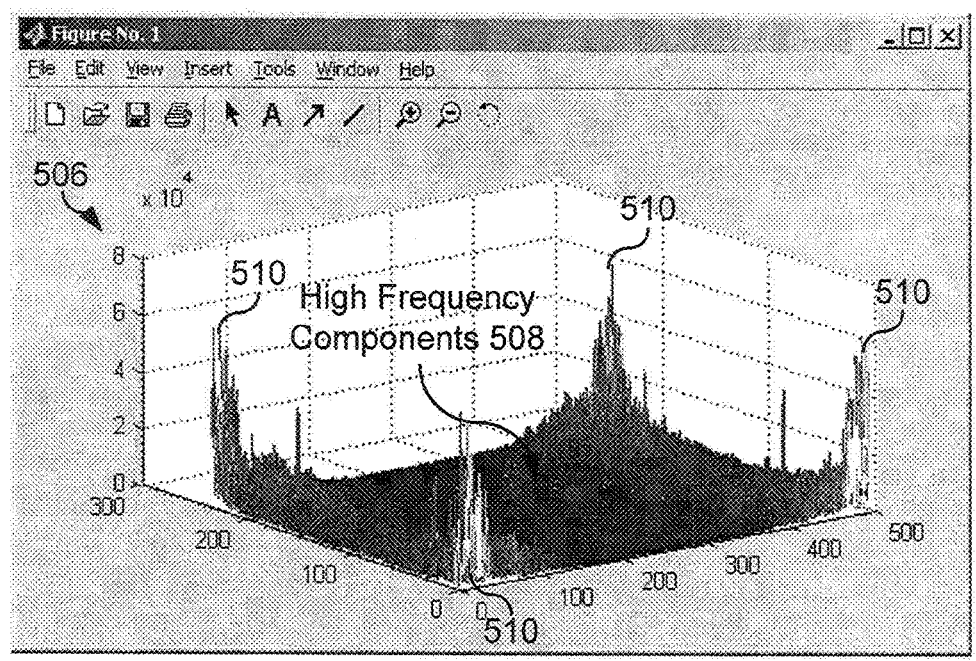
FIGS. 5B, 6B, 7B, 8B, and 9B provide the corresponding Fast Fourier Transform ("FFT")
Figure 6A:
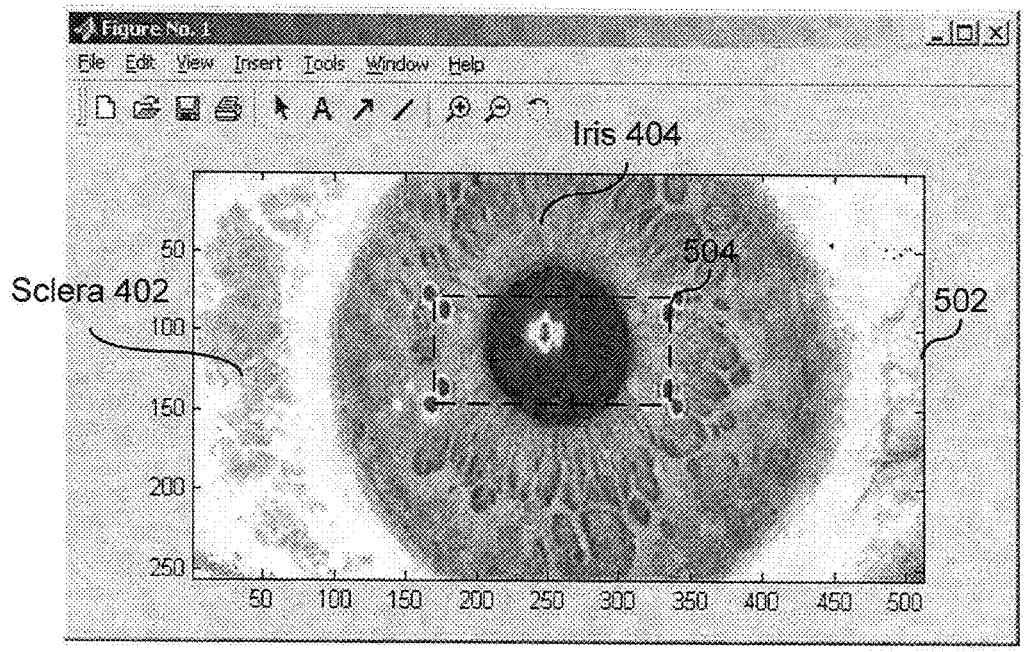
Figure 6B:
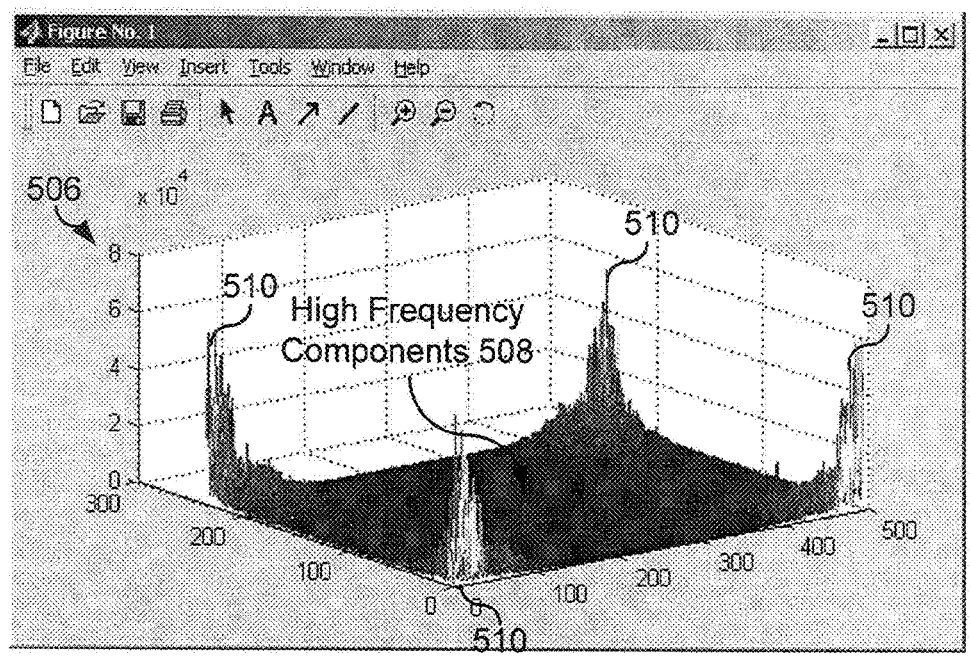
Figure 7A:
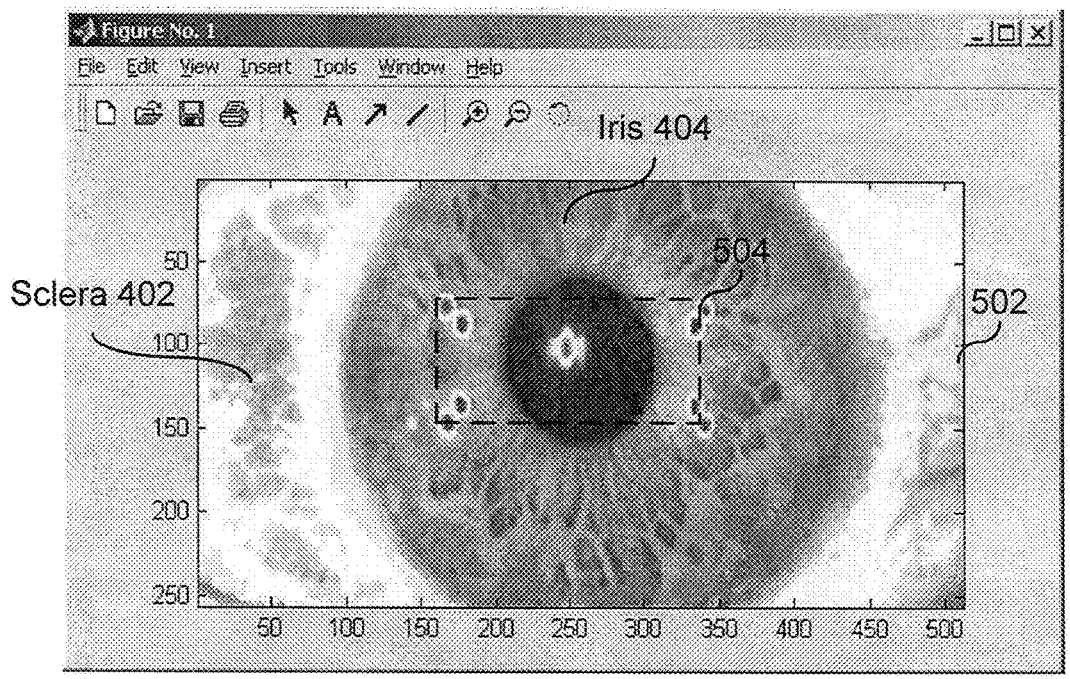
Figure 7B:
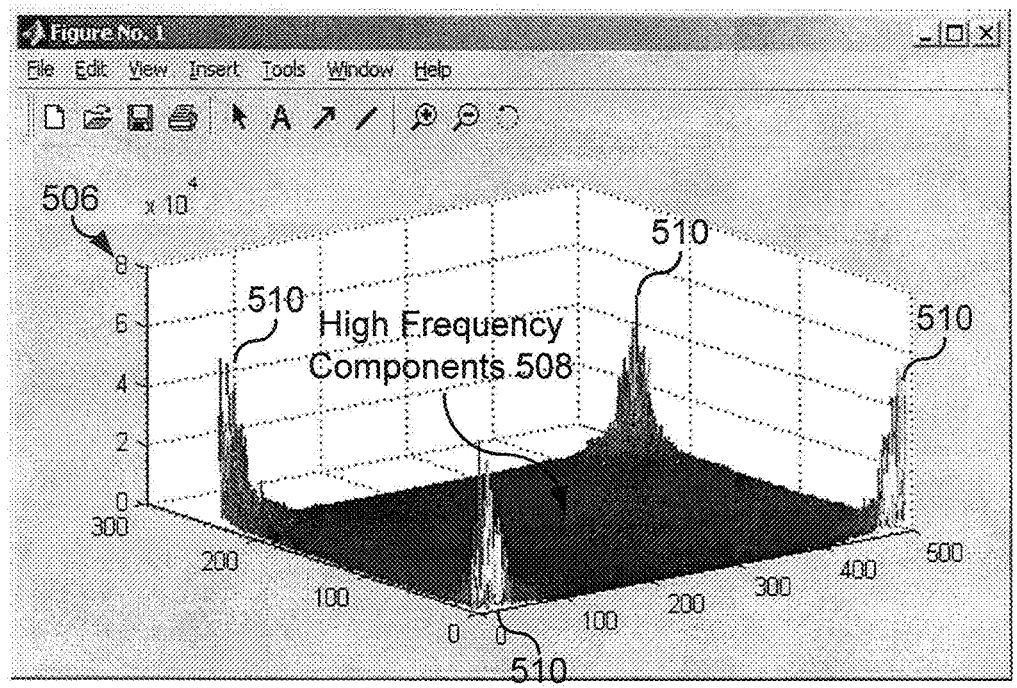
Figure 8A:
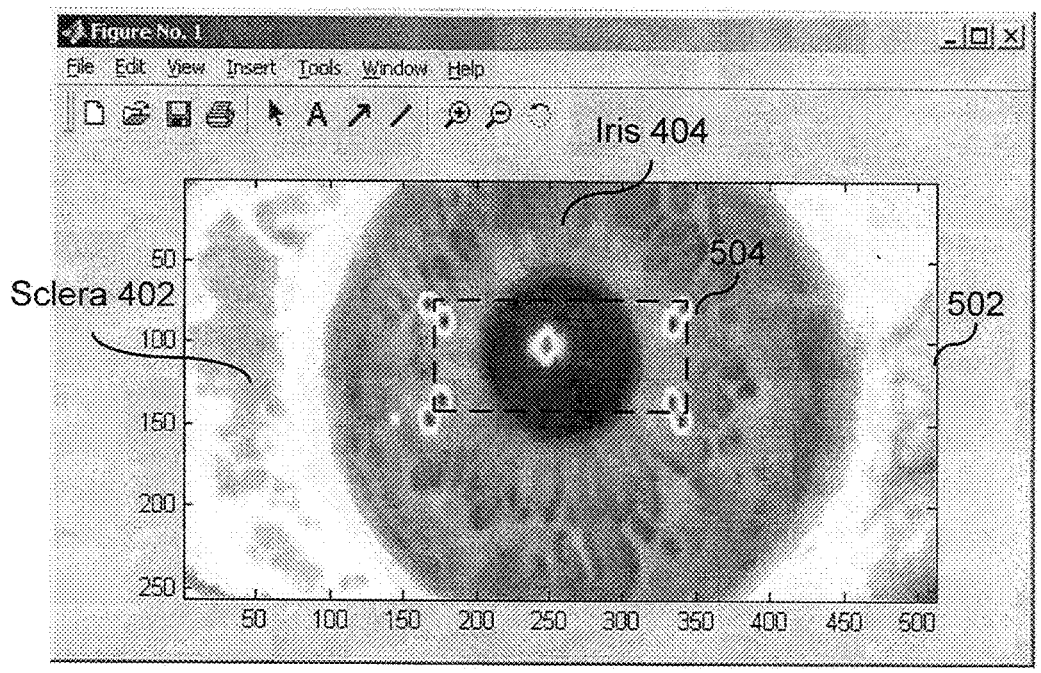
Figure 8B:
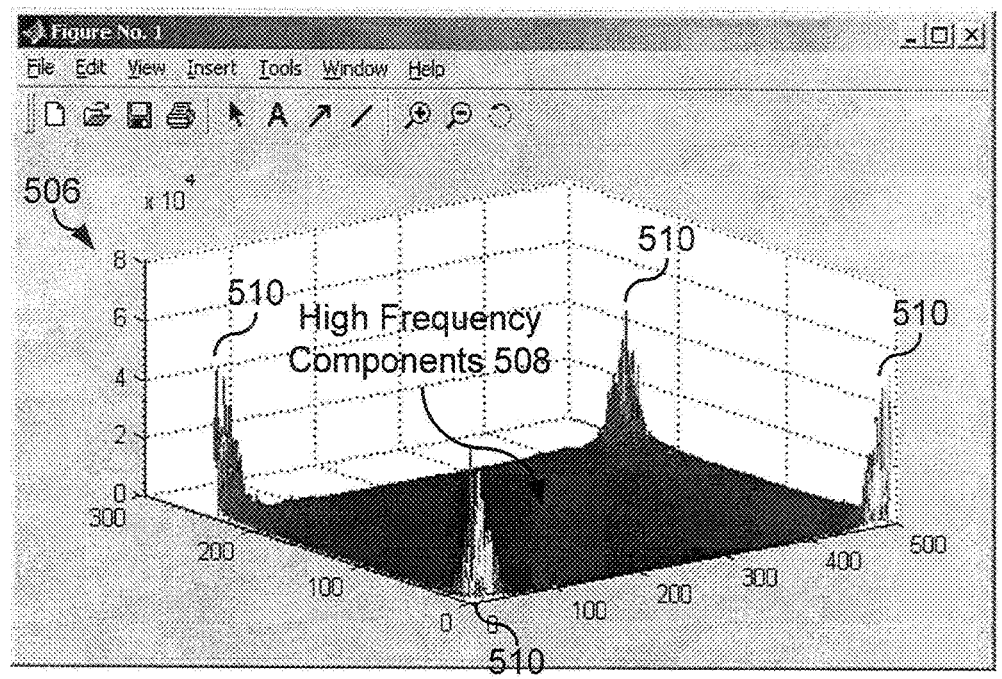
Figure 9A:
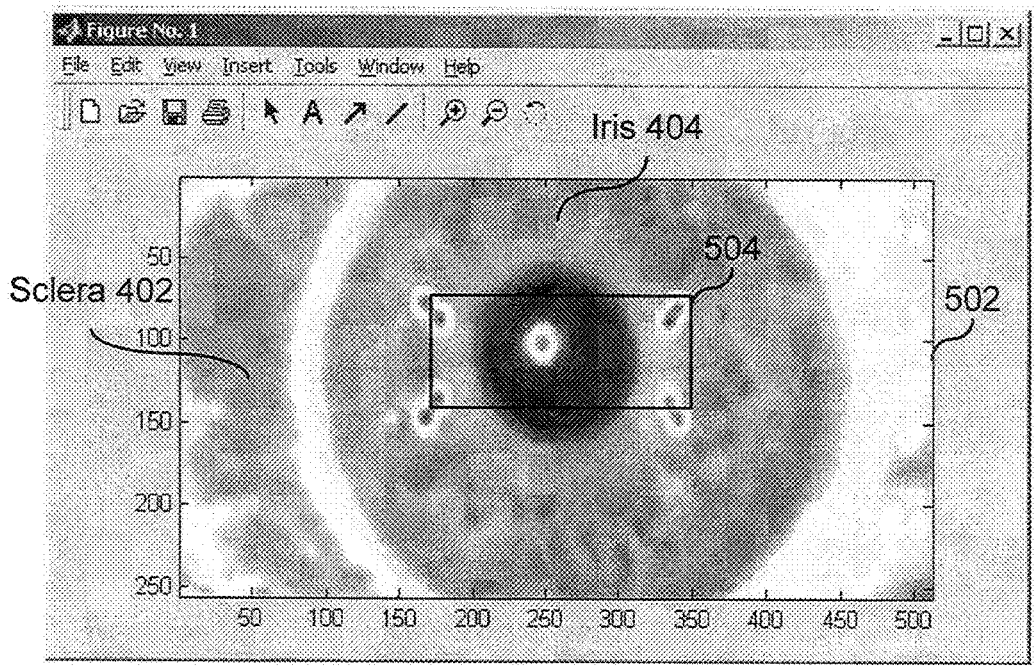
Figure 9B:
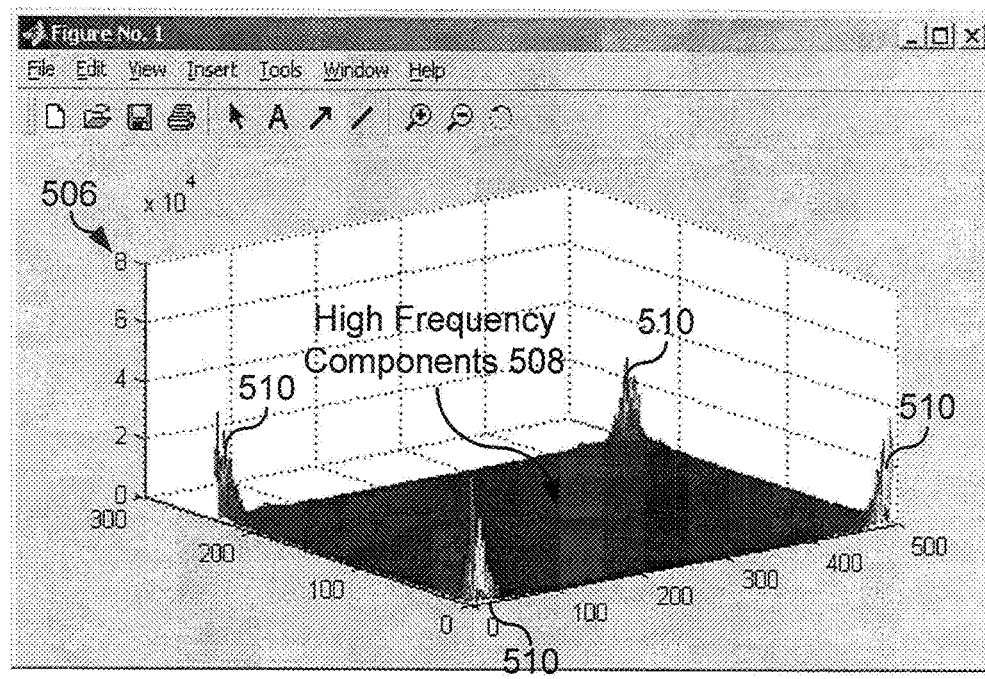

FIG. 4 shows a typical image of an eye 10 captured on a wavefront sensor. This eye is well focused and sclera 402 and iris 404 features are clearly visible. FIGS. 5A, 6A, 7A, 8A and 9A mimic the effect of defocus caused by having the eye in the wrong position. These images are blurred to varying levels as will occur when the image is out of focus.

A region of interest is selected from each image 502. A substantially similar area or region may be used within each image. In this case a rectangular area 504 that did not contain eyelids or eyelashes was extracted from each image. Note that multiple regions could be used, such as different regions on the sclera (for example, to the left and right and above and below the sclera), regions from the iris, or combinations of these. Note also that more sophisticated algorithms for selecting the area(s) of interest could potentially also automatically eliminate artifacts in the image, such as the images of light sources.

Two-dimensional FFT were performed on each of the blurred images. The dominant feature in the FFT's is the DC value and those values close to DC. These features are of no interest in this processing (other than, potentially, for normalizing the data). FIGS. 5A, 6A, 7A, 8A and 9A are pseudo-color plots of each of the images, The sharpest image is FIG. 5A. FIGS. 6A, 7A, 8A, and 9A are increasingly blurred. FIGS. 5B, 6B, 7B, 8B, and 9B provide the corresponding FFT's. The FFT sizes used were 256 by 512 although other size FFTs could be used. In these plots the data close to DC has been eliminated so as to make the medium and higher frequency content more visible. In plots 506, where the highest frequency components 508 are in the center, one can observe that, as the image becomes more blurred, the plots 506 become flatter away from the corners 510 (i.e. there is less information at the medium and higher frequencies). Thus by comparing the high frequency content one can identify the image having the greatest focus.

A refinement to this approach is the application of a harmonic windowing function (such as a Hamming window) to the region(s) of interest prior to the FFT. In addition to the typical benefit of the reduction of harmonic artifacts that is achieved from such an operation, this may reduce sensitivity to slight decentration or shift of the region(s) that could result from uncompensated eye movement. This benefit would be achieved since data near the periphery of the region(s) would be maximally attenuated by the windowing function.

Figure 10:
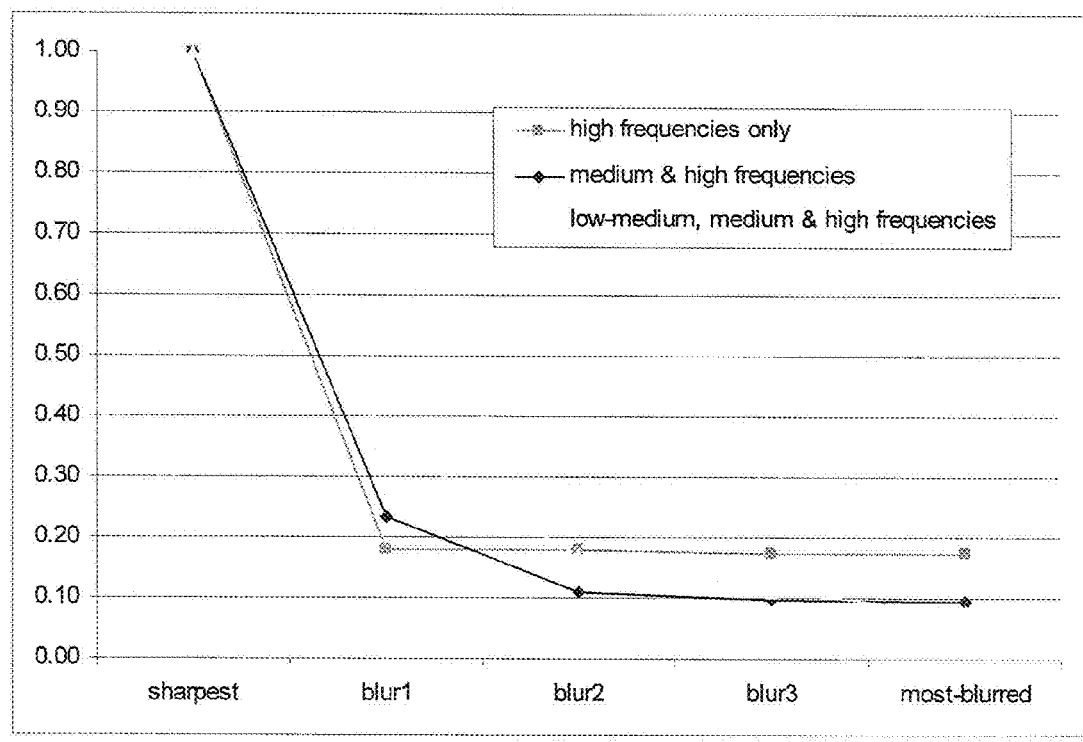
FIG. 10 plots metrics that have been computed as the integral over the FFT in accordance with an embodiment of the present invention.

FIG. 10 plots metrics that have been computed as the integral over the FFT from some lower frequency out to the maximum frequency in the data. The lower frequency values were varied so as to increase or decrease the amount of data used in computing the integral. These metrics were normalized so as to have a peak value of 1.0 in the plot provided. One can clearly see that when only the highest frequency components are used the metric is extremely sensitive to even minor amounts of blurring. This allows for precisely determining when the object (eye) is in best focus. However, this metric cannot be used to discriminate between images with different but modest levels of blur because the value becomes effectively constant after even a small amount of blur. The integrals that included lower frequencies show differences for each image at higher levels of blur and so could be used to discriminate between more blurred images, but are also less sensitive for the minimal blur case. Optimal metrics, therefore, account for this type of variation and combine information from different frequencies (straight integration is just one of many possible approaches) such that they can be used to discriminate between both large and small levels of blur.

Figure 11:
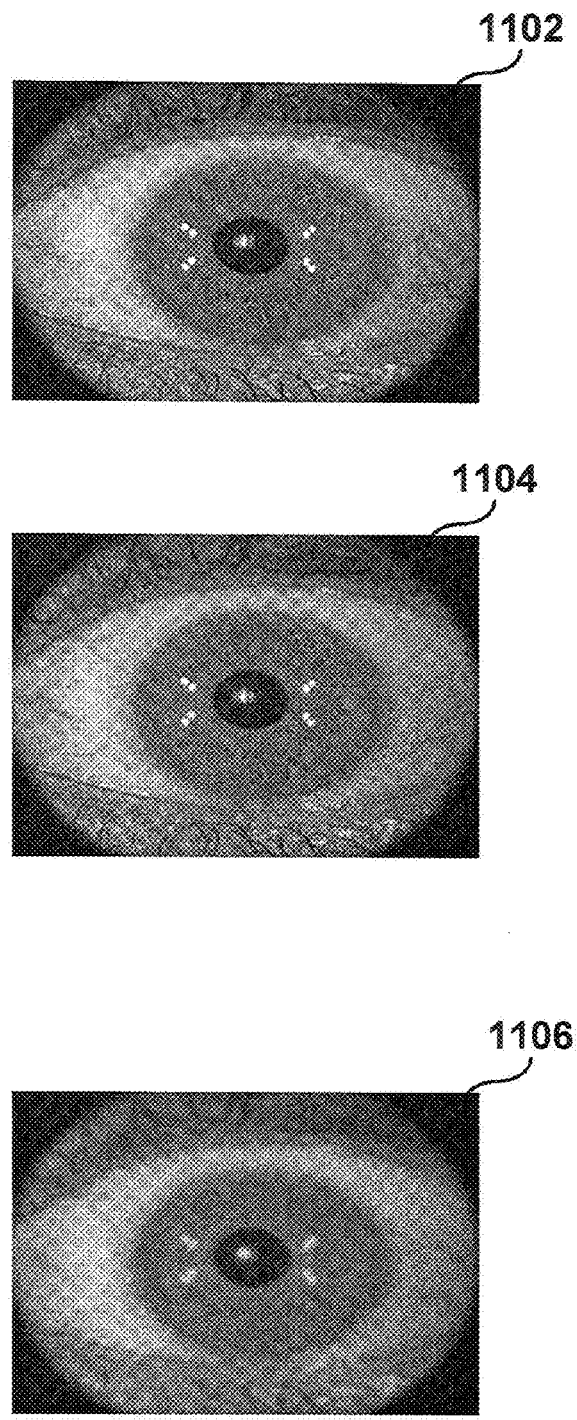
FIGS. 11A, 11B and 11C provided three full images in gray-scale to better illustrate just how little difference there appears to be between the optimally focused and minimally blurred images.

FIGS. 11A, 11B and 11C provided three full images 1102, 1104, and 1106 in gray-scale to better illustrate just how little difference there appears to be between the optimally focused and minimally blurred images. This shows the extreme sensitivity of this approach when looking at just higher frequency information. Also FIG. 11C shows the maximally blurred case from these examples.

The example presented here shows how the post-FFT data has the information necessary to facilitate optimal device-to-eye positioning. Optimal initial positioning of the device can be achieved by maximizing sharpness metrics. If there is also intent to display the positioning error in units of length, make use of the information during a procedure to adjust device-to-eye distance, or potentially pause a procedure, then a calibration step may well be necessary. For example, by varying the device-to-eye distance a small, known amount around optimal prior to commencing the procedure, it may be possible to relate spectral (post-FFT) information to distance errors.

Figure 12:
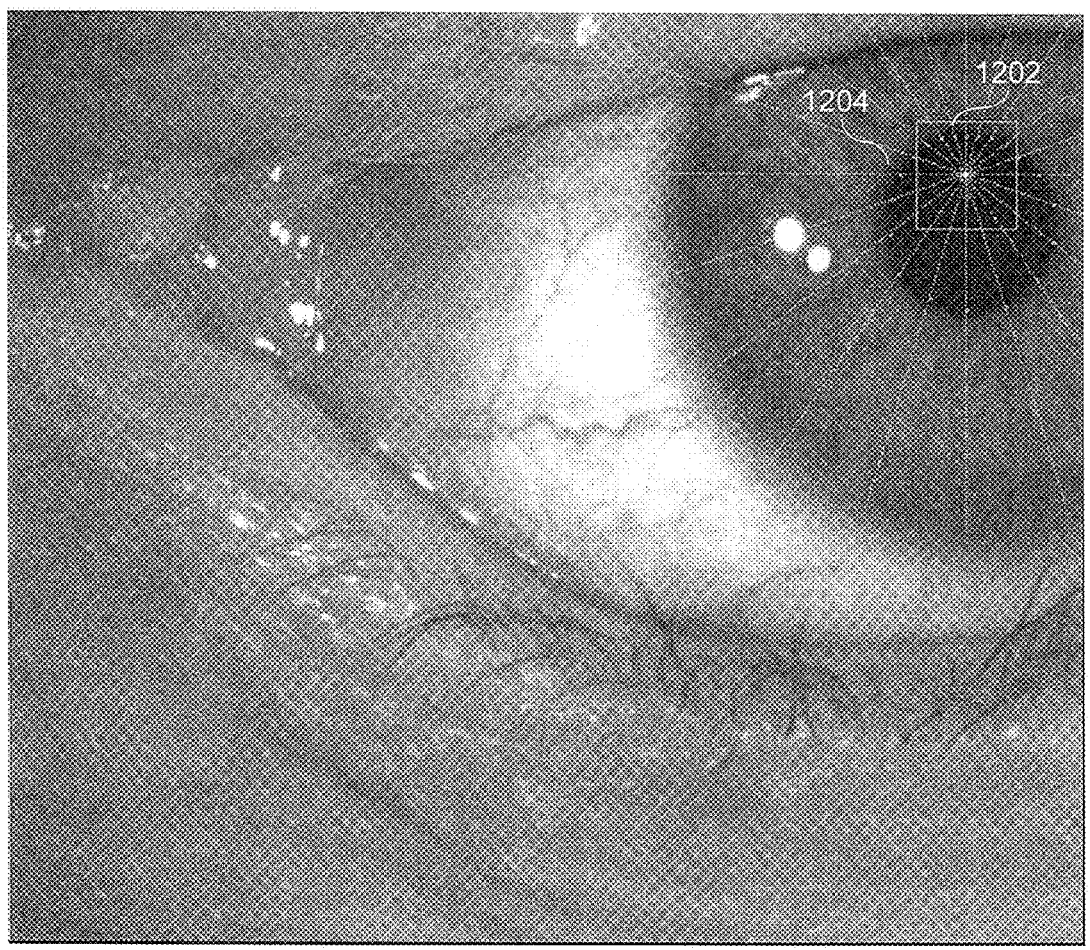
FIG. 12 depicts determining pupil center from all of the pupil boundary points in accordance with an embodiment of the present invention.
Figure 13:
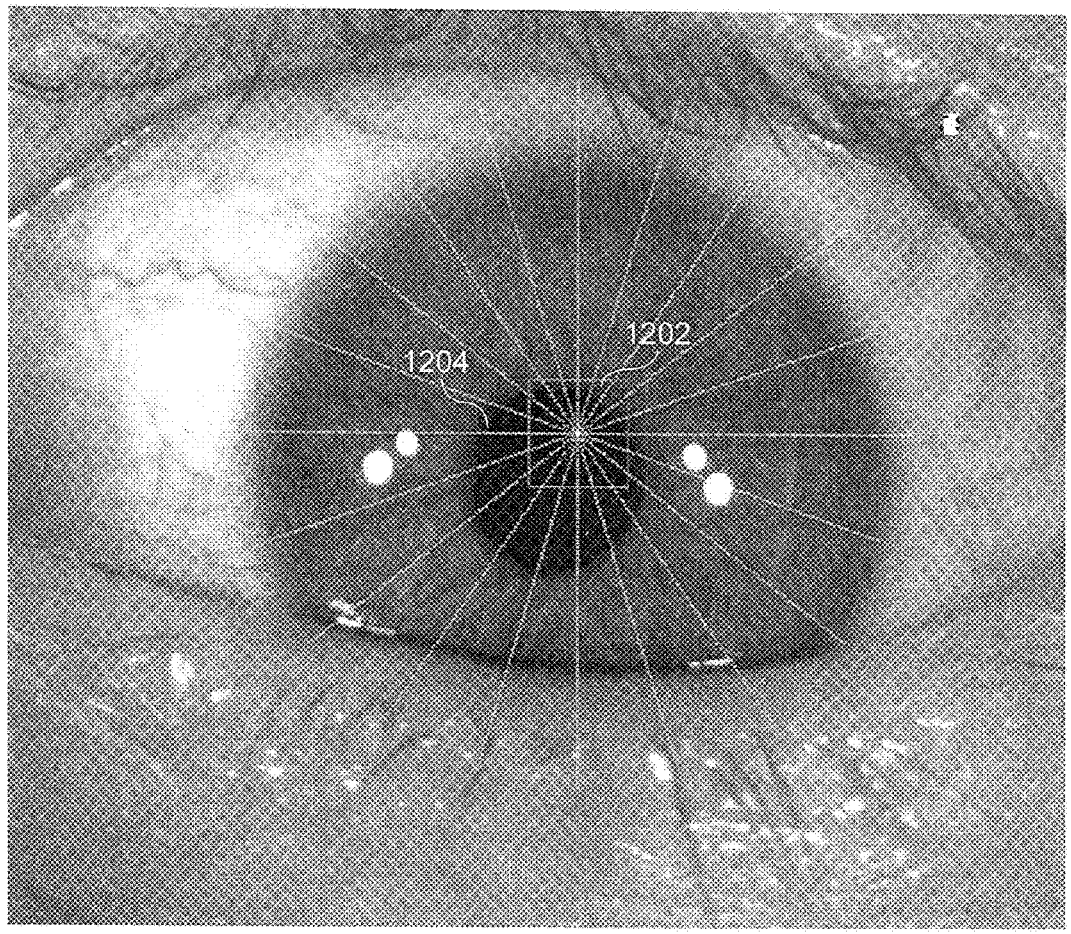
FIG. 13 depicts the pupil being in the center of the field of view in accordance with an embodiment of the present invention.

One method of pupil location detection is accomplished by performing a few simple steps. The software algorithm first scans the image to determine the location of the darkest region via summing the pixel values in a rectangle 1202 of appropriate size (for example 1.5 mm square). This rectangle 'window' is then slid across the image, scanning every row until the entire image has been scanned. The 'window' with the smallest sum is considered the darkest region of the image, and therefore the approximate location of the pupil 1204. Then, the algorithm scans outward from the center of the rectangle, looking for a pixel value threshold change along 'n' radial lines to determine the pupil boundary. The pupil center is determined from all of the pupil boundary points as shown in FIG. 12. Once the pupil center is located, the ophthalmic device and/or patient can be repositioned until the pupil 1204 is located in the center of the field of view, as shown in FIG. 13.

Embodiments of the present invention substantially address misalignments associated with a refractive treatment performed using a laser, such as an Excimer laser.

Positioning of ophthalmic devices, such as alignment of the laser vision correction laser beam, may be employed between individual patients or procedures associated with an individual patient. Therefore, the laser beam may be aligned between the procedure on a patient's first eye and his second eye. Other circumstances may arise that require the realignment of the laser vision correction laser beam, such as a change in the pulse repetition rate of the laser. This ensures that the laser is aligned at the frequency with which the laser vision correction procedure is to be performed.

Embodiments of the present invention provide a system and method operable to position an ophthalmic device relative to an eye that substantially addresses the above identified needs as well as other needs. One embodiment provides a method which first obtains a series of images of an eye. In these series of images, the distance between the ophthalmic device and the eye is varied while the region of the eye image remains substantially the same. The images are then processed to determine a high frequency content or sharpness function associated with each image. By comparing the high frequency content associated with each image, the image having the largest amount of high frequency content or highest sharpness function is identified. The high frequency content or sharpness function varies with the focus of the image. An optimally focused image will have the largest amount of high frequency content or highest function. By identifying the image associated with the highest frequency content or sharpness function from the series of images, the relative position or distance between the eye and the ophthalmic device having the largest amount of high frequency content (i.e., optimally focused) is identified. This distance may be used to position the ophthalmic device relative to the patient's eye.

Embodiments of the present invention advantageously provide an accurate and repeatable alignment mechanism. The time associated with a manual geometry adjust or other like calibration is greatly reduced or eliminated between patients. This reduced setup time allows alignment to be performed between treatment of eyes of a bilateral case without any additional time penalty.

Additionally, the embodiments of the present invention may be used to automatically compensate for system misalignments from a variety of sources without requiring external mechanisms. Other aspects of the present invention may help maintain a stable operating temperature within the beam scanning mechanism in order to further reduce fluctuations in system performance. This invention can be used to efficiently assist in setting optimal focus or distance between an ophthalmic device and an eye. In cases where the device has motorized capability that allows for setting of the distance between the device and an eye, the embodiments of this invention can be used in a closed-loop manner to automatically set the distance to the desired value. When such automated capabilities do not exist, the embodiments of this invention can be used to generate cues to the operator (e.g. via a GUI) to assist in the manual operation.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described.

What is claimed is:

1. A method of positioning a laser vision correction device relative to an eye, the method comprising:
    obtaining a series of images, wherein each image is of a same region of the eye, wherein the eye and the laser vision correction device are separated by a different distance for each image;
    determining a high frequency content associated with each image;
    comparing the high frequency content associated with each image to determine which image has the largest amount of high frequency content; and
    adjusting the relative position between the laser vision correction device and the eye to the distance associated with the image having the largest amount of high frequency content.

2. The method of claim 1, wherein image focus is optimized with the image having the largest amount of high frequency content.

3. The method of claim 1, wherein a sharpness function is performed on the series of images to quantify the high frequency content associated with each image.

4. The method of claim 3, wherein the sharpness function comprises at least one function selected from the group comprising:

estimation of image gray level variance and amplitude;

computation of an intensity difference between adjacent pixels of an image;

standard edge-detection functions; and

Fourier transforms.

5. The method of claim 1, wherein positioning the laser vision correction device comprises automatically positioning the laser vision correction device as directed by a computer control system.

6. The method of claim 1, wherein positioning the ophthalmic device comprises automatically positioning the eye as directed by a computer control system.

7. The method of claim 1, further comprising adjusting a relative position of the eye with a field of view of the laser vision correction device.

8. The method of claim 1, wherein the region comprises an iris boundary.

9. A method of focusing a laser vision correction device relative to an eye, the method comprising:

obtaining a series of images, wherein each image is of a region of the eye, wherein the eye and the laser vision correction device are separated by a different distance for each image;

determining a sharpness function associated with each image;

comparing the sharpness function associated with each image to determine which image has the highest sharpness function; and adjusting the relative position between the laser vision correction device and the eye to the distance associated with the image having the highest sharpness function, and wherein image focus is optimized with the image having the highest sharpness function.

10. The method of claim 9, wherein the sharpness function comprises at least one function selected from the group comprising:

estimation of image gray level variance and amplitude;

computation of an intensity difference between adjacent pixels of an image;

standard edge-detection functions; and

Fourier transforms.

11. The method of claim 9, wherein positioning the laser vision correction device comprises automatically positioning the laser vision correction device as directed by a computer control system.

12. The method of claim 9, wherein positioning the ophthalmic device comprises automatically positioning the eye as directed by a computer control system.

* * * * *